(12) United States Patent
Pierre et al.

(10) Patent No.: US 8,535,649 B2
(45) Date of Patent: Sep. 17, 2013

(54) COSMETIC COMPOSITION INCLUDING AN ANHYDROUS GEL AND A GLYCERYL ESTER

(75) Inventors: Stephanie Pierre, Paris (FR); Michele Mousset, Nogent sur Marne (FR); Celine Carles, Paris (FR)

(73) Assignee: Chanel Parfums Beaute, Neuilly sur Seine (FR)

( * ) Notice: Subject to any disclaimer, the term of this patent is extended or adjusted under 35 U.S.C. 154(b) by 427 days.

(21) Appl. No.: 12/747,327

(22) PCT Filed: Dec. 10, 2008

(86) PCT No.: PCT/EP2008/067187
§ 371 (c)(1),
(2), (4) Date: Jun. 10, 2010

(87) PCT Pub. No.: WO2009/074599
PCT Pub. Date: Jun. 18, 2009

(65) Prior Publication Data
US 2010/0272663 A1  Oct. 28, 2010

Related U.S. Application Data

(60) Provisional application No. 61/015,244, filed on Dec. 20, 2007.

(30) Foreign Application Priority Data

Dec. 10, 2007 (FR) ...................... 07 59691

(51) Int. Cl.
*A61K 8/90* (2006.01)
*A61K 8/92* (2006.01)

(52) U.S. Cl.
USPC ............. 424/64; 424/401; 424/70.1; 514/558

(58) Field of Classification Search
USPC .......................................... 424/424, 64, 70.1
See application file for complete search history.

(56) References Cited

U.S. PATENT DOCUMENTS

| 5,221,534 | A | 6/1993 | DesLauriers et al. |
| 2004/0137028 | A1 | 7/2004 | De La Poterie |
| 2006/0008489 | A1* | 1/2006 | Egawa et al. .................. 424/401 |
| 2006/0051307 | A1* | 3/2006 | Gotou et al. ................ 424/70.11 |

FOREIGN PATENT DOCUMENTS

| EP | 1857092 A | 11/2007 |
| FR | 2785530 A | 5/2000 |
| FR | 2816500 A | 5/2002 |
| JP | 2007277115 A | * 10/2007 |

OTHER PUBLICATIONS

Hayama, A., "Oily Cosmetic" JP 2007-277115A, Oct. 2007, machine translation.*
International Search Report in Corresponding Application No. PCT/EP2008/067187 dated Apr. 14, 2009.

* cited by examiner

*Primary Examiner* — Gina C Justice
(74) *Attorney, Agent, or Firm* — Young & Thompson

(57) ABSTRACT

The present invention relates to a cosmetic composition including, in a physiologically acceptable medium: (a) at least 30% by weight of an anhydrous gel having a viscosity of at least 180 000 cP-s at 25° C. which includes at least one oil and at least one copolymer of styrene and at least one olefin other than styrene; (b) at least one specific glycerol diester; and (c) optionally at most 10% by weight of wax(es), the composition exhibiting a phase shift δ between its elastic modulus (G') and its viscous modulus (G') of less than 45° at a frequency of 30 to 50 Hz. It also relates to a cosmetic method for caring for or making up the lips, including the topical application to the lips of the abovementioned composition.

15 Claims, 2 Drawing Sheets

COSMETIC COMPOSITION INCLUDING AN ANHYDROUS GEL AND A GLYCERYL ESTER

Figure 1:
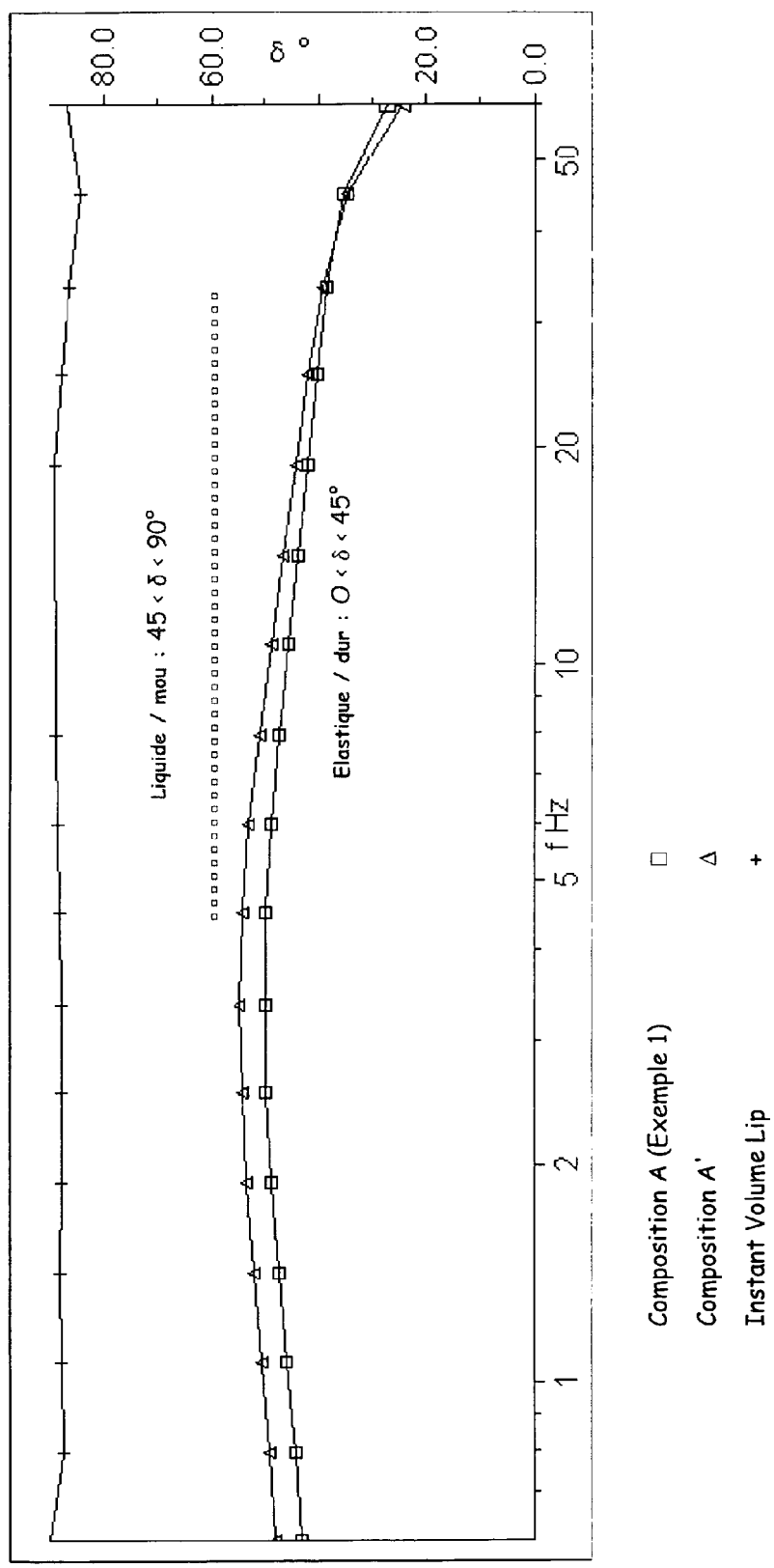

The present invention relates to a cosmetic composition. It also relates to a cosmetic method for caring for or making up the lips, comprising the topical application to the lips of this composition.

Among compositions for making up the lips, glosses denote generally fluid, transparent to opalescent, compositions intended to contribute gloss to the lips by the use of certain oils having a high refractive index. These oils are structured or gelled by waxes or oily gelling agents, making it possible to adjust the viscosity of the composition. The compositions thus obtained are generally packaged in a container, such as a small bottle provided with an applicator, generally a fine brush made of foam.

It is known that the use of a high level of conventional waxes, which makes it possible to obtain a thick film and good hold of the makeup, has several disadvantages, in particular the difficulty of obtaining transparent or translucent compositions, and also exhibits problems of recrystallization of the waxes, which are capable of affecting the stability of these compositions and of reducing the lifetime of the applicator. In order to overcome this problem, the Applicant Company had the idea of replacing the greater part of these waxes by the combination of a specific glycerol ester with an anhydrous gel, composed of a mixture of olefinic copolymers in hydrogenated polyisobutene. A gel of this type has in particular already been described in U.S. Pat. No. 6,309,629 as improving the resistance of glosses to migration into the fine lines around the lips. In addition, a gloss including the abovementioned combination exists on the market. However, it has been observed by the Applicant Company that the gloss formulations comprising this combination of structuring agents generate threads on exiting from the small bottle, during the withdrawal of the composition by the applicator. It is to the credit of the Applicant Company to have succeeded in overcoming this problem of threading capable of detrimentally affecting the preciseness of the line without affecting the hold of this gloss, without loss of glossiness. The gloss thus obtained has also proven to be less tacky than that of the prior art.

In order to do this, the specific glycerol ester mentioned above has been combined with an anhydrous gel of the abovementioned type but of higher viscosity. Such an ester has in particular already been described in application US 2006/0008489 as gelling agent for oily makeup products, including in particular branched hydrocarbons, but it has never, to the knowledge of the Applicant Company, been used in combination with an anhydrous gel formed of olefinic copolymers of high viscosity.

A subject matter of the present invention is thus a cosmetic composition comprising, in a physiologically acceptable medium:

(a) at least one anhydrous gel having a viscosity of at least 180 000 cP·s at 25° C. which includes at least one oil and at least one copolymer of styrene and at least one olefin other than styrene;

(b) at least one ester obtained from: (i) a saturated or unsaturated and linear or branched aliphatic acid or hydroxy acid having from 8 to 30 carbon atoms, (ii) a linear or branched diacid having from 12 to 36 carbon atoms, and (iii) glycerol or a glycerol condensate; and (c) optionally at most 10% by weight of wax(es), said composition exhibiting a phase shift δ between its elastic modulus (G') and its viscous modulus (G'') (such that tan δ=G''/G') of less than 45° at a frequency of 30 to 50 Hz.

The above ingredients are combined in proportions which make it possible to obtain a composition exhibiting the abovementioned phase shift between its elastic modulus (G') and its viscous modulus (G'') and thus a greater elastic modulus (G') than its viscous modulus (G'') at a frequency of 30 to 50 Hz at ambient temperature. The Applicant Company has shown that these rheological characteristics make it possible to obtain compositions which do not form threads under conditions corresponding to the shearing applied by the consumer during the withdrawal of the composition from a small bottle using a fine brush.

These ingredients will now be described in more detail.

Copolymer of Styrene and of Olefin

The copolymers present in the anhydrous gel used according to the invention are preferably block copolymers. They include, in addition to the styrene, at least one olefin which can be chosen from: ethylene, propylene, butylene, butadiene and isoprene, without this list being limiting. It can thus be a copolymer sold by Shell under the trade name Kraton®, which can in particular be a styrene-ethylenepropylene, styrene-ethylenebutylene, styrene-butadiene, styrene-isoprene, styrene-butadiene-styrene, styrene-isoprene-styrene or styrene-ethylenebutylene-styrene copolymer or also an ethylene/propylene/styrene or butylene/ethylene/styrene copolymer or any blend of the abovementioned copolymers, for example a blend of ethylene/propylene/styrene and butylene/ethylene/-styrene copolymers.

It is preferable, according to the invention, to use an ethylene/propylene/styrene or butylene/ethylene/styrene copolymer or their blends.

These copolymers are generally sold in dispersion in at least one oil chosen from, for example: a volatile or nonvolatile hydrocarbon, such as a mineral oil, hydrogenated polyisobutene, hydrogenated polydecene, isohexadecane or isododecane; or a fatty acid ester, such as isopropyl palmitate or isononyl isononanoate; or a benzoic acid ester. It is preferable, according to the invention, for the copolymer of styrene and of olefin to be conveyed in hydrogenated polyisobutene.

An example of a blend of copolymers which can be used according to the invention is composed of the Dekagel® products sold by Jan Dekker and in particular Dekagel® HV2004.

Preferred copolymers for use in the present invention are those sold by Penreco under the trade names Versagel® M, ME, ML, MP, MC, MD and MN. Those of the ME series are particularly preferred.

These copolymers advantageously have a weight-average molecular weight ranging from 50 000 to 260 000. In addition, the anhydrous gel in which they are present has a viscosity at 25° C., measured with a Brookfield viscosimeter using the T-C spindle at 5 revolutions/min, after conditioning at rest for three days at ambient temperature, which is greater than 180 000 cP·s, preferably greater than 200 000 cP·s, more preferably greater than 220 000 cP·s, better still greater than 240 000 cP·s, such as a viscosity of approximately 250 000 cP·s.

It is particularly preferable to use the copolymer sold by Penreco under the trade name Versagel® ME 2000.

The anhydrous gel (a) can represent from 30 to 80% by weight, preferably from 40 to 70% by weight, more preferably from 50 to 65% by weight, with respect to the total weight of the composition. The copolymer present therein can thus represent from 4.5 to 12% by weight, preferably from 6 to 10.5% by weight, more preferably from 7.5 to 9.75% by weight, with respect to the total weight of the composition.

Glyceryl Ester

The composition according to the invention includes, as second essential constituent, at least one ester obtained from: (i) a saturated or unsaturated and linear or branched aliphatic acid or hydroxy acid having from 8 to 30 and preferably from 12 to 22 carbon atoms, (ii) a linear or branched diacid having from 12 to 36 and preferably from 12 to 20 carbon atoms, and (iii) glycerol or a glycerol condensate.

The aliphatic acid (i) can be chosen in particular from lauric acid, myristic acid, palmitic acid, oleic acid, stearic acid, 12-hydroxystearic acid, behenic acid and their mixtures. In addition, the diacid (ii) can, for example, be chosen from eicosanedioic acid, ethyl-octadecanedioic acid, dodecanedioic acid and their mixtures.

A glyceryl ester of this type which is preferred for use in the present invention is the diester of eicosanedioic acid and of glycerol esterified with behenic acid. This compound is an ester of formula RO—$CH_2$—CH(OR)—$CH_2$—O—CO—$(CH_2)_{18}$—CO—O—$CH_2$—CH(OR)—$CH_2$—OR, where the R groups independently denote a —CO—$(CH_2)_{20}$—$CH_3$ or H group, provided that at least one of the R groups is other than H, or a mixture of such esters. It is available in particular from Nisshin Oillio under the trade name Nomcort® HK-G.

The ester (b) can represent from 0.1 to 5% by weight, preferably from 0.2 to 3% by weight, more preferably from 0.5 to 2% by weight, with respect to the total weight of the composition.

Waxes

The term "wax" is understood to mean a fatty substance which exhibits a reversible liquid/solid change in state, which has a melting point of greater than 30° C. and generally of less than 90° C., which is liquid under the conditions of preparation of the composition and which exhibits, in the solid state, an anisotropic crystalline arrangement. The waxes used according to the invention can be composed of polar or nonpolar waxes or of a mixture of the two. The term "nonpolar" is understood to mean a wax which includes only carbon, hydrogen and/or phosphorus atoms and in particular a hydrocarbon.

Examples of nonpolar waxes are in particular paraffin, polymethylene, polyethylene or polypropylene waxes or waxes formed of ethylene/propylene copolymer, micro-crystalline waxes, ozokerite and their mixtures. Examples of such waxes are sold in particular by Sasol Wax under the trade name Sasol Wax® C80, by Jeen under the trade names Jeenate® 2H to 6H and by New Phase under the trade names Performalene® 500 and Performa® V343.

The polar waxes can be chosen in particular from animal waxes, vegetable waxes and synthetic or silicone waxes including polar groups, such as esters. Mention may thus be made of carnauba wax, candelilla wax, beeswax (Cera alba), Chinese insect wax (*Ericerus pela*), Japan wax, sumac wax, montan wax, triesters of $C_8$-$C_{20}$ acids and of glycerol, such as glyceryl tribehenate, acetylated glycol stearate, sold in particular by Vevy under the trade name Cetacene®, and their mixtures.

These waxes can in particular be used in the form predispersed in an oil, as is the case with the mixture of candelilla wax and of jojoba seed oil sold by Ina Trading under the trade name Green Grease®.

It is preferable, according to the invention, to use a nonpolar wax, in particular a polyethylene wax.

The above constituents (a) to (c) are conveyed in the fatty phase of the composition according to the invention, which can be an anhydrous composition or an emulsion, in particular a water-in-oil (W/O) emulsion.

As well as these constituents, the fatty phase can include at least one oil, in addition to that present in the olefinic copolymer gel, which can be identical to or different from the latter.

Within the meaning of the present invention, the term "oil" is understood to mean a compound which is liquid at ambient temperature (25° C.) and which, when it is introduced in a proportion of at least 1% by weight into water at 25° C., is not at all soluble in water or soluble to a level of less than 10% by weight, with respect to the weight of oil introduced into the water.

The oils which can be used in the composition according to the invention can be chosen from: hydrocarbon oils; synthetic (poly)esters and (poly)ethers, in particular (poly)esters of $C_6$-$C_{20}$ acids and of $C_6$-$C_{20}$ alcohols which are advantageously branched, such as isononyl isononanoate; vegetable oils; branched and/or unsaturated fatty acids; branched and/or unsaturated fatty alcohols, such as octyldodecanol; silicone oils, such as linear polydimethylsiloxanes, which are optionally phenylated, or cyclic polydimethylsiloxanes; fluorosilicone oils; fluorinated oils; and their mixtures.

The amount of additional oil present in the composition according to the invention preferably represents from 10 to 50%, more preferably from 20 to 40%, of the total weight of this composition.

Among these oils, it is preferable to use, in the present invention, at least one glossy oil, that is to say an oil exhibiting a refractive index of greater than 1.45 and preferably of greater than 1.47.

Examples of glossy oils are in particular hydrocarbon oils, such as polybutene, hydrogenated polyisobutene or hydrogenated polydecene, and also phenylated silicone oils, such as those identified by the INCI name "phenyl trimethicone", an example of which is composed of the silicone available under the trade name Mirasil® PTM from Rhodia, those identified by the INCI name "phenylpropyldimethylsiloxysilicate", an example of which is composed of the silicone available under the trade name Silshine® 151 from General Electric, and those identified by the INCI name "trimethyl pentaphenyl trisiloxane", an example of which is composed of the silicone available under the trade name DC PH® 1555 HRI from Dow Corning.

Mention may also be made, as glossy oils, of the fluorinated silicones identified by the INCI name "perfluorononyl dimethicone", an example of which is composed of the silicone available under the trade name Pecosil® FS (FSU, FSL, and the like) from Phoenix and another example of which is composed of the silicone available under the trade name Biosil Basics® (Fluorosil LF, 14, and the like) from Biosil Technologies.

Other examples of glossy oils are natural oils and in particular castor seed oil; mono- and polyesters of fatty acids and/or of fatty alcohols, the fatty chain of which includes from 6 to 20 carbon atoms, in particular: mono- and polyesters of hydroxy acids and of fatty alcohols, such as diisostearyl malate, esters of benzoic acid and of fatty alcohols, such as $C_{12}$-$C_{15}$ alkyl benzoate, polyesters of polyols and in particular of (di)pentaerythritol, such as pentaerythrityl tetraisostearate, dipentaerythrityl pentaisononanoate and dipentaerythrityl $C_5$-$C_9$ esters, or of polyglycerol, such as that known under the INCI name "bis-diglyceryl polyacyladipate-1" and sold by Sasol under the trade name Softisan® 645, or of trimethylolpropane, such as trimethylolpropane triethylhexanoate, which is sold in particular by Kokyu Alcohol Kogyo under the trade name Kak® TTO, or of propylene glycol, such as propylene glycol dibenzoate, which is sold in particular by Inolex under the trade name Lexfeel Shine®, and isocetyl stearoyl stearate; and polyesters of hydrogenated castor oil, such as the esters sold by Kokyu Alcohol Kogyo under the trade names Risocast® DA-H and Risocast® DA-L.

It is clearly understood that the composition according to the invention can comprise mixtures of the oils mentioned above.

The composition according to the invention can in addition advantageously comprise from 50% to 100% by weight, for example from 60 to 100% by weight and preferably from 70% to 100% by weight of glossy oil, with respect to the total weight of the oils present in the composition.

The fatty phase of the water-in-oil emulsion according to the invention can in addition advantageously include at least one structuring agent for a fatty phase, other than the constituents (a) to (c) described above, such as a lipophilic gelling agent.

Examples of lipophilic gelling agents are in particular silicone polymers and more particularly organopoly-siloxane elastomers. Mention may be made, among these, of the at least partially crosslinked polymers resulting from the reaction of an organopolysiloxane or of a polyether carrying unsaturated groups, such as vinyl or allyl groups, preferably situated at the end of the chain, with another reactive silicone compound, such as an organohydropolysiloxane. These polymers are usually available in gel form in a volatile or non-volatile silicone solvent or in a hydrocarbon solvent. Examples of such elastomers are sold in particular by Shin-Etsu under the trade names KSG-6, KSG-16, KSG-31, KSG-32, KSG-41, KSG-42, KSG-43, KSG-44, KSG-21 and KSG-210, by Dow Corning under the trade names DC 9040 and DC 9041 and by Grant Industries under the trade name Gransil®. Another oily gelling agent is composed of a silicone polymer, obtained by self-polymerization in the presence of a catalyst of an organopolysiloxane functionalized by epoxy groups and hydrosilylated, which is available commercially from General Electric under the trade name Velvesil® 125. Another lipophilic gelling agent is composed of a cyclic vinyl-dimethicone/dimethicone copolymer, such as that sold by Jeen under the trade name Jeesilc® PS (including PS-VH, PS-VHLV, PS-CM, PS-CMLV and PS-DM). Another type of lipophilic gelling agent is composed of polyamides, such as those identified by the INCI name polyamide-3 and in particular the Sylvaclear® AF 1900V and PA 1200V polymers available from Arizona Chemical, and also those identified by the INCI name "Ethylene-diamine/Hydrogenated Dimer Dilinoleate Copolymer Bis-Di-C14-18 Alkyl Amide" and available, for example, under the trade name Sylvaclear® A200V or Sylvaclear® A2614V from Arizona Chemical. In an alternative form, the lipophilic gelling agent can be a bentone or a sucrose ester, such as that denoted by the INCI name "Sucrose tetrastearate triacetate".

The fatty phase can also include one or more pasty compounds, that is to say lipophilic fatty substances which, like the waxes, are capable of undergoing a reversible liquid/solid change in state and have, in the solid state, an anisotropic crystalline arrangement but which differ from the waxes in that they include, at a temperature of 23° C., a liquid fraction and a solid fraction.

In addition, it can comprise at least one film-forming polymer capable of introducing hold and/or transfer-free properties and/or gloss to the makeup conferred by the composition. It can in particular be a silicone polymer optionally modified by urethane or fluorine or acrylate, such as the (meth)acrylate silicones sold by Shin-Etsu under the trade names KP-545, KP-561 and KP-562, or the polymers sold by Dow Corning under the trade names DC FA 4002 ID and DC FA 4001 CM. Other examples of film-forming polymers are silicone resins and in particular MQ resins, such as trimethyl-siloxysilicates, and MT resins, such as silsesquioxane derivatives and in particular polymethyl-silsesquioxanes, sold in particular by Shin-Etsu, and also the polypropylsilsesquioxane sold by Dow Corning under the trade name DC 670 or the phenyl-propylpolysilsesquioxane sold by Wacker under the trade name Belsil SPR45VP. Another example is composed of fluorosilicone polymers identified by the INCI name "Trifluoro-propyldimethylsiloxy Triethylsiloxysilicate", such as that sold by General Electric under the trade name XS66-B8226. Use may also be made, as film-forming polymers, of bioadhesive polymers obtained, for example, by polycondensation of dimethiconol and of MQ silicate resin in a solvent, such as heptane, which are sold in particular by Dow Corning under the trade names DC7-4405 low tack and DC7-4505 high tack. Other examples of film-forming polymers are poly(cyclic olefins), such as polycyclopentadiene, sold in particular by Kobo under the trade name Koboguard 5400, or also polydicyclopentadiene. Yet other examples of film-forming polymers are composed of copolymers of vinylpyrrolidone (VP) and/or of linear olefins, such as VP/hexadecene and VP/eicosene copolymers, including Antaron V216 and Antaron V220 from ISP, or also ethylene/vinyl acetate copolymers, such as AC 400 from Baerlocher. Mention may also be made of polyethers, such as poly(vinyl stearyl ether), sold in particular by Phoenix under the trade name Giovarez® 1800. Other film-forming polymers capable of being used in this invention are polyacrylates, such as poly(ethyl acrylate), sold in particular by Creations Couleurs under the trade name Creasil 7 ID.

It is preferable for the composition according to the invention to be anhydrous.

However, in the case where it is provided in the form of an emulsion, the composition according to the invention includes, in addition to the fatty phase described above, an aqueous phase comprising water and optionally hydrophilic and/or water-soluble additives.

In this case, the composition according to the invention includes from 5 to 30% by weight, preferably from 10 to 20% by weight, of water, with respect to the total weight of the composition.

For greater transparency, the refractive index of the aqueous phase can advantageously be enhanced by providing for the aqueous phase to include at least one polyol, and in particular by a sugar.

In addition to water and the possible polyols described above, the aqueous phase of the emulsion can comprise hydrophilic active principles, hydrophilic latexes and/or hydrophilic gelling agents.

The composition according to the invention can also comprise one or more emulsifiers, in particular water-in-oil emulsifiers, preferably chosen from non-ionic surfactants, such as polyethoxylated dipolyhydroxystearate (30 EO), sold in particular under the trade name Arlacel® P135 by Uniqema; or polyglyceryl polyesters, such as polyglyceryl-4 diisostearate/polyhydroxystearate/sebacate (Isolan GPS® from Gold-schmidt); or also polysiloxanes modified by polyethers, without this list being limiting.

The composition used according to the invention can additionally include at least one filler. This term is understood to mean any inorganic or organic particle of any shape (in particular spherical or lamellar) which is insoluble in the composition. Examples of fillers are talc, mica, silica, kaolin, boron nitride, starch, starch modified by octenylsuccinic anhydride, polyamides, silicone resins, powders derived from silicone elastomers and powders derived from acrylic polymers, in particular from poly(methyl methacrylate). The fillers can in particular be composed of several layers of different chemical nature and/or of different physical form and can in particular be provided in the form of lamellae coated with spherical fillers. They can be modified using various surface treatments. An example of a surface-treated filler is composed of silica modified by an ethylene/methacrylate copolymer, sold in particular by Kobo under the trade names DSPCS® 20N-I2, 3H-I2 and I2.

The composition can also comprise at least one coloring material chosen from water-soluble or fat-soluble dyes, fillers having the effect of coloring and/or opacifying the composition and/or of coloring the lips, such as pigments, pearlescent agents, lakes (water-soluble dyes adsorbed on an inert inorganic carrier), and their mixtures. These coloring materials can optionally be treated at the surface with a hydrophobic agent, such as silanes, silicones, fatty acid soaps, $C_{9-15}$ fluoroalkyl phosphates, acrylate/dimethicone copolymers, mixed $C_{9-15}$ fluoroalkyl phosphate/silicone copolymers, lecithins, carnauba wax, polyethylene, chitosan and optionally acylated amino acids, such as lauroyl lysine, disodium stearoyl glutamate and aluminum acyl glutamate. The pigments can be inorganic or organic and natural or synthetic. Examples of pigments are in particular iron, titanium or zinc oxides, and also composite pigments and goniochromatic, pearlescent, interference, photochromic or thermochromic pigments, without this list being limiting. Examples of pigments which can be used in the composition according to the invention are hemispherical composite pigments manufactured from crosslinked poly(methacrylic acid) methyl ester and from organic dyes. Such composite pigments are sold in particular by Daito Kasei. The pearlescent agents can be chosen from those conventionally present in makeup products, such as mica/titanium dioxide products. In an alternative form, they can be pearlescent agents based on mica/silica/titanium dioxide, based on synthetic fluorphlogopite/titanium dioxide (Sunshine® from Maprecos), based on calcium sodium borosilicate/titanium dioxide (Reflecks® from Engelhard) or based on calcium aluminum borosilicate/silica/titanium dioxide (Ronastar® from Merck).

Advantageously, when it includes one or more pigments, the composition according to the invention additionally comprises at least one dispersant, such as butylene glycol cocoate or diisostearyl malate.

The composition according to the invention can also include one or more sweetening agents, such as sorbitol, sucrose, xylitol, acesulfame-K and sodium saccharinate; antioxidants, such as ascorbic acid and/or its alkyl or phosphoryl esters, or also tocopherol and its esters; sequestering agents, such as EDTA salts; pH adjusters; preservatives; and fragrances.

It can in addition comprise at least one UV screening agent chosen from organic and inorganic screening agents and their mixtures. Mention may in particular be made, as organic screening agents, of dibenzoylmethane derivatives (including butyl methoxydibenzoylmethane), cinnamic acid derivatives (including ethylhexyl methoxycinnamate), salicylates, para-aminobenzoic acids, β,β-diphenylacrylates, benzophenones, benzylidenecamphor derivatives, phenylbenzimidazoles, triazines, phenylbenzotriazoles and anthranilic derivatives. Mention may in particular be made, as inorganic screening agents, of screening agents based on inorganic oxides in the form of pigments or nanopigments which may or may not be coated and in particular based on titanium dioxide or on zinc oxide.

Examples of such adjuvants are mentioned in particular in the CTFA dictionary (International Cosmetic Ingredient Dictionary and Handbook published by The Cosmetic, Toiletry and Fragrance Association, 9th Edition, 2002).

Preferably, the composition employed according to the invention is used as product for making up the lips, for example as lip gloss.

Another subject matter of the present invention is thus a cosmetic method for caring for or making up the lips, comprising the topical application to the lips of the composition as described above.

The invention will now be illustrated by the following nonlimiting examples.

EXAMPLES

Example 1

Lip Gloss

A lip gloss was manufactured in a way conventional to a person skilled in the art, which lip gloss has the following composition in which the proportions of the ingredients are expressed as percentages by weight:

| Ingredient INCI name/type | Amount |
|---|---|
| Hydrogenated polyisobutene & ethylene/propylene/styrene copolymer & butylene/ethylene/styrene copolymer | 60.00% |
| Octyldodecanol | 10.00% |
| Bis-diglyceryl polyacyladipate-1 | 5.00% |
| Polybutene | 8.00% |
| Preservatives | 0.40% |
| Diisostearyl malate | 13.90% |
| Phytantriol | 0.20% |
| Glyceryl behenate/eicosanedioate | 1.50% |
| Ground pigments | 0.30% |
| Antioxidants | 0.70% |

Example 2

Rheological Evaluation

The viscoelastic behavior of various formulations was evaluated on a Gemini rheometer at 20° C. in an unsaturated atmosphere, the device being used in controlled strain (1%) dynamic mode and equipped with plate/plate geometry with a gap of 1000 μm. The top plate was driven with an oscillatory movement around its axis with a frequency sweep from 0.6 to 60 Hz.

The strain of the composition generated a torque transmitted to a sensor. A comparison of the controlled strain signal and of the transmitted torque was carried out via a processing signal and sent to a calculator which made it possible to access the elastic modulus and the viscous modulus (or loss modulus) of the sample and also the loss angle.

The formulations studied corresponded:
Composition A: to the composition of example 1
Composition A': to a composition similar to composition A but including other ground pigments
Composition B: to a composition similar to composition A but comprising only 26.90% by weight of olefinic copolymer gel Versagel® ME2000

Composition A": to a composition similar to composition A but not including glyceryl behenate/eicosanedioate, compensated for by antioxidants Instant Volume Lip: to a lipstick sold by Deborah, including an anhydrous gel formed of copolymer of styrene and of olefin having a viscosity at 25° C. of 160 000 cP·s, and also Nomcort® HK-G.

Figure 2:
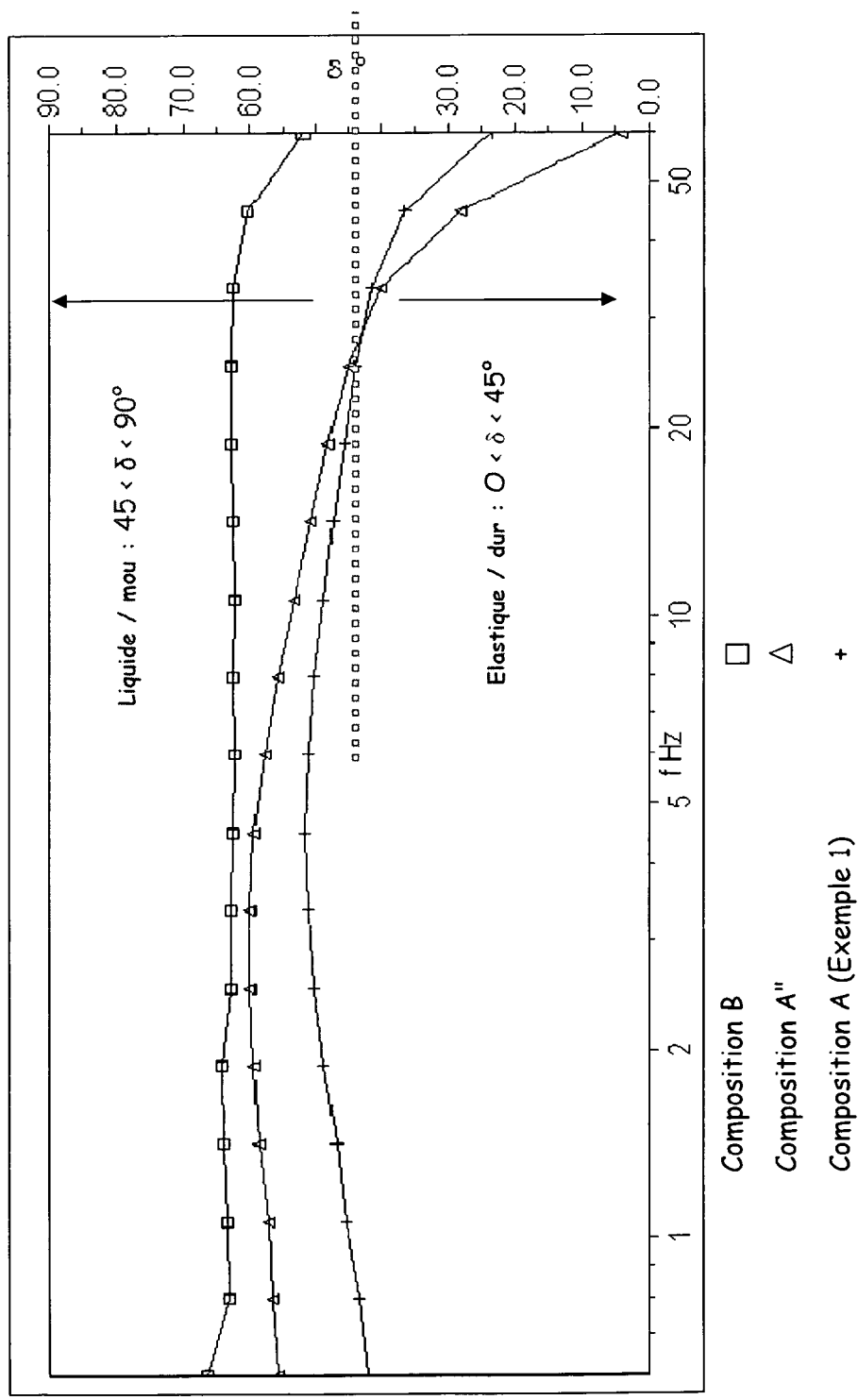

The results obtained are illustrated:

in FIG. 1, from which it emerges that compositions A and A' exhibited a loss angle of less than 45° beyond approximately 15 and 20 Hz respectively, while the composition of the prior art always exhibited a loss angle of much greater than 45°; and in FIG. 2, which shows that compositions A and A" exhibited a loss angle of less than 45° beyond approximately 25 Hz, while composition B always exhibited a loss angle of much greater than 45°.

It results, from this evaluation, that the use of an anhydrous gel formed of olefinic copolymer with an excessively low viscosity (Instant Volume Lip) or in an insufficient amount (composition B) does not make it possible to obtain a composition having a loss angle of less than 45° at most 30 Hz.

Example 3

Sensory Evaluation

The sensory profile of composition A of example 1 was compared with a composition C including 27.45% of anhydrous gel formed of olefinic copolymer Versagel® ME750 (viscosity: 100 000 cP·s at 25° C.), 3.3% of Nomcort® HK-G and 48.10% of polybutene. These compositions were each packaged in a small bottle and then evaluated by a trained panel of 15 subjects under standardized conditions of temperature, hygrometry and light.

In order to do this, each small bottle was first placed standing upright on a table and the composition present therein was removed from the small bottle by pulling all at once on the applicator. The formation of a peak after removal reflected the threading nature of the composition.

Various cosmetic properties of each composition were subsequently evaluated on application (slip, freshness, softness, thickness of the deposit layer) and then after application (sharpness of the outline, homogeneity, opaqueness, intensity of color, glossiness, glitter and pearlescent effects, tackiness, softness of the lips, presence on the lips, threading).

It was observed that composition C was much more threading and that it was also more tacky than composition A according to the invention. The two compositions in addition exhibited similar characteristics of glossiness and of hold.

The Applicant Company has demonstrated that the threading nature of these compositions resulted directly from their viscoelastic behavior as described in example 2, a composition with a smaller loss angle being more elastic and a composition exhibiting a viscous modulus greater than its elastic modulus continuing to form threads even when it is rapidly stressed (at a high frequency).

What is claimed is:

1. A cosmetic composition comprising, in a physiologically acceptable medium:
   (a) from 30 to 80% of the weight of the composition of at least one anhydrous gel having a viscosity of at least 180 000 cP·s at 25° C. which includes at least one oil and at least one copolymer of styrene and at least one olefin other than styrene;
   (b) at least one ester obtained from: (i) a saturated or unsaturated and linear or branched aliphatic acid or hydroxy acid having from 8 to 30 carbon atoms, (ii) a linear or branched diacid having from 12 to 36 carbon atoms, and (iii) glycerol or a glycerol condensate; and
   (c) optionally at most 10% by weight of wax(es), said composition exhibiting a phase shift δ between its elastic modulus (G') and its viscous modulus (G") of less than 45° at a frequency of 30 to 50 Hz.

2. The composition as claimed in claim 1, wherein said olefin is selected from the group consisting of: ethylene, propylene, butylene, butadiene and isoprene.

3. The composition as claimed in claim 1, wherein said copolymer is a copolymer selected from the group consisting of: ethylene-propylene-styrene, butylene-ethylene-styrene, styrene-butadiene, styrene-isoprene, styrene-butadiene-styrene, styrene-isoprene-styrene, styrene-ethylenebutylene-styrene and their blends.

4. The composition as claimed in claim 3, wherein said copolymer is a blend of ethylene-propylene-styrene and butylene-ethylene-styrene copolymers.

5. The composition as claimed in claim 1, wherein the oil is a hydrocarbon oil.

6. The composition as claimed in claim 1, wherein the anhydrous gel has a viscosity of at least 200 000 cP·s.

7. The composition as claimed in claim 1, wherein the aliphatic acid (i) is selected from the group consisting of lauric acid, myristic acid, palmitic acid, oleic acid, stearic acid, 12-hydroxystearic acid, behenic acid and their mixtures.

8. The composition as claimed in claim 1, wherein the diacid (ii) is selected from the group consisting of eicosanedioic acid, ethyloctadecanedioic acid, dodecanedioic acid and their mixtures.

9. The composition as claimed in claim 1, wherein the ester (b) is a diester of eicosanedioic acid and of glycerol esterified with behenic acid.

10. The composition as claimed in claim 1, wherein the anhydrous gel (a) represents from 40 to 70% of the weight of the composition.

11. The composition as claimed in claim 1, wherein the ester (b) represents from 0.1 to 5% of the weight of the composition.

12. The composition as claimed in claim 1, wherein the wax is selected from the group consisting of: paraffin, polymethylene, polyethylene or polypropylene waxes or waxes formed of ethylene/propylene copolymer, microcrystalline waxes, ozokerite, carnauba wax, candelilla wax, beeswax (Cera alba), Chinese insect wax (Ericerus pela), Japan wax, sumac wax, montan wax, triesters of $C_8$-$C_{20}$ acids and of glycerol, and their mixtures.

13. The composition as claimed in claim 1, which is anhydrous.

14. The composition as claimed in claim 1, which exhibits a greater elastic modulus (G') than its viscous modulus (G") at a frequency of 30 to 50 Hz.

15. A cosmetic method for caring for or making up the lips, comprising the topical application to the lips of the composition as claimed in claim 1.

* * * * *

UNITED STATES PATENT AND TRADEMARK OFFICE
CERTIFICATE OF CORRECTION

PATENT NO. : 8,535,649 B2  Page 1 of 1
APPLICATION NO. : 12/747327
DATED : September 17, 2013
INVENTOR(S) : Pierre et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 430 days.

Signed and Sealed this

Fifteenth Day of September, 2015

Michelle K. Lee
*Director of the United States Patent and Trademark Office*